(12) United States Patent
Yoon et al.

(10) Patent No.: US 7,514,265 B2
(45) Date of Patent: Apr. 7, 2009

(54) ALDEHYDE DETECTION KIT AND METHOD THEREOF

(75) Inventors: Min Jin Yoon, Kyunggi-Do (KR); Joong Cheol Lee, Incheon (KR); Yang Seo Ku, Seoul (KR)

(73) Assignee: Marine Products Tech, Kyunggi-Do (KR)

(*) Notice: Subject to any disclaimer, the term of this patent is extended or adjusted under 35 U.S.C. 154(b) by 727 days.

(21) Appl. No.: 10/959,482

(22) Filed: Oct. 5, 2004

(65) Prior Publication Data

US 2006/0073604 A1    Apr. 6, 2006

(51) Int. Cl.
*G01N 21/78* (2006.01)
*C08K 5/16* (2006.01)
*C09B 11/10* (2006.01)

(52) U.S. Cl. .............. 436/128; 436/130; 436/166; 436/100; 436/102; 436/119; 436/122; 106/493

(58) Field of Classification Search ......... 436/122, 436/128, 100, 102, 119, 130; 260/391; 106/493; 552/110
See application file for complete search history.

(56) References Cited

U.S. PATENT DOCUMENTS

| | | | | |
|---|---|---|---|---|
| 3,386,788 A | * | 6/1968 | Dreyer | 359/242 |
| 4,753,891 A | * | 6/1988 | Thompson et al. | 436/130 |
| 4,816,177 A | * | 3/1989 | Nelson et al. | 252/181 |
| 4,824,610 A | * | 4/1989 | Sappok et al. | 552/114 |
| 5,593,491 A | * | 1/1997 | Karnell | 106/493 |
| 6,165,797 A | | 12/2000 | Halstead | |
| 6,689,617 B1 | | 2/2004 | Abels | |

\* cited by examiner

*Primary Examiner*—Duane S Smith
*Assistant Examiner*—Ives Wu
(74) *Attorney, Agent, or Firm*—Joseph Hyosuk Kim; JHK Law

(57) ABSTRACT

The present application describes a reagent system for detecting presence of aldehyde in a sample that includes (i) Component A, which includes bisulfite, pararosalinine, and hydrochloric acid; and (ii) Component B, which includes a solution of hydroxide, wherein the Component A has a pH of from about 1.4 to 1.6.

16 Claims, No Drawings

US 7,514,265 B2
ALDEHYDE DETECTION KIT AND METHOD THEREOF

BACKGROUND OF THE INVENTION

1. Field of the Invention

The present invention relates to a reagent system that can be used to detect aldehyde in biological specimens. The invention also relates to production of a test kit utilizing the reagent system, and various applications of the test kit.

2. General Background and State of the Art

Research has shown that the amount of oxygen free radicals present in the body correlates to the degree of exposure to stress, ultraviolet light, and extraneous forms of pollution. It is known that when oxygen free radicals, which are byproducts of metabolic activities, oxidize long chain polyunsaturated fatty acids within the body, aldehydes are released. Different types of aldehydes, including malondialdehyde, 4-Hydroxynonenal, acetaldehyde, 1-propanal, 2-methylpropanal, 2,2-dimethylpropanal, 1-butanal, 1-pentanal, and n-hexanal, are created during this process. Such forms of aldehydes, due to their strong reactivity, cause many health complications by altering the structure of proteins and mutating nucleic acids. Therefore, it is desirable to measure the amount of aldehydes, which may indicate the extent of the presence of oxygen free radicals in the body.

Malondialdehyde is a natural component of urine. Its presence can be detected by using a fuchsin testing kit or a spectrophotometer, fluorometer, HPLC or GC-MS. Reagents of conventional fuchsin based testing kits had to be stored in acidic conditions and tested in acidic environments. For example, U.S. Pat. No. 6,689,617 presents a fuchsin based test kit comprising sodium metabisulfite, distilled water, phosphorus, and fuchsin that uses a reagent of between 1.75-1.93 pH to detect malondialdehyde in urine. In U.S. Pat. No. 6,165,797, another test kit composed of acetic acid, sodium bisulfite, distilled water, phosphorus and distilled water is presented.

Basic fuchsin, which is a purple powder, alters its color relative to the amount of aldehyde present in an acidic environment. The amino group of fuchsin couples with the aldehyde to produce a pink to purple color approximately dependent on the amount of aldehyde present in biological fluids such as blood or urine. Conventional test kits that use basic fuchsin require acidic environments for the color alteration to be executed; thus the accuracy of test results is compromised during the process of combining fuchsin with biological specimen (generally of higher pH), which dilute the concentration of malondialdehyde and cause the reaction process to be dependent on the pH of the environment. In addition, the fuchsin used in conventional reagents become unstable when exposed to heat, leading to a quick deterioration in the effectiveness of the reagents.

Thus, there is a need in the art for the development of a reagent that remains stable in heat and which test accuracy is less affected by the pH of its surroundings. By using a test solution containing a detection compound in the pararosaniline HCl family, which reacts to aldehydes by creating a solution of different color, which also exhibits stability towards heat and acidic conditions when stored, the shortcomings of conventional aldehyde test kits are overcome.

SUMMARY OF THE INVENTION

The present invention is directed to a stable aldehyde detection reagent system.

The present invention is directed to a reagent system for detecting the presence of aldehyde in a sample comprising: (i) Component A, which comprises bisulfite, pararosaniline HCl, and hydrochloric acid; and (ii) Component B, which comprises a solution of hydroxide, wherein the Component A has a pH of from about 1.4 to 1.6. In one aspect, the bisulfite may be sodium bisulfite and may be present in an amount of about 1 to 20 grams per liter of Component A.

In the reagent system, pararosaniline HCl may be present in a range of about 1 to 10 grams per liter of Component A. And the hydrochloric acid may be present in about 0.017 to 1 mole per liter of Component A.

In the reagent system the hydroxide may be sodium hydroxide and may be present in about 0.1 to 10 grams per liter of water in Component B.

In the reagent system described above, preferably the aldehyde to be detected may be malondialdehyde. And further, the preferred sample may be blood or urine.

In another aspect, the invention is directed to a reagent solution for detecting the presence of aldehyde in a test sample comprising bisulfite, pararosaniline HCl, hydrochloric acid and hydroxide, wherein the pH of the solution is neutral. The bisulfite may be sodium bisulfite and may be present in about 0.5 to 10 grams per liter of reagent solution. Further, the reagent solution may include pararosaniline HCl in about 0.5 to 5 grams per liter of reagent solution.

In another aspect of the invention, the invention is directed to a kit for detecting the presence of aldehyde in a test sample comprising: (i) at least one reagent container that contains the contents of Components A and B described above; (ii) a container for collecting the test sample; (iii) a sample transfer device for transferring a portion of the sample from the container to another container for reaction with the reagent solution; and (iv) a color table to be referred to for comparison with the color of the reaction.

In this kit, the contents of Component A and Component B may be contained together in one container. Alternatively, the contents of Component A and contents of Component B may be contained in separated containers. In particular, the kit may include from about 0.2 to 2 ml of Component A and about 0.2 to 2 ml of Component B contained in the reagent container. Further, Components A and B may be present in a 1:0.8~1.2 volume ratio, respectively.

The present invention is also directed to a method for detecting the presence of aldehyde in a test sample comprising (i) making a reagent solution containing contents of Components A and B as described above; (ii) contacting the sample with the reagent solution obtained in (i) to form a reaction; and (iii) determining the presence of the aldehyde in the sample by comparing the color of the reaction with a color table. The sample to be tested in this method may be blood or urine. In this method, the reaction may take place in neutral pH. The reaction color may be read at between about 2 to 7 minutes, preferably 5 minutes. Moreover, the form of aldehyde to be measured may be malondialdehyde.

DETAILED DESCRIPTION OF THE PRESENT INVENTION

In the present application, "a" and "an" are used to refer to both single and a plurality of objects.

As used herein, "aldehyde" has its ordinary chemical meaning and the inventive assay is used to detect such aldehyde group bearing compound. In particular, various forms of aldehydes include without limitation malondialdehyde, 4-hydroxynonenal, acetaldehyde, 1-propanal, 2-methylpropanal, 2,2-dimethylpropanal, 1-butanal, 1-pentanal, and n-hexanal.

As used herein, "neutral pH" refers to a pH range within about 6.5 to 7.5.

As used herein, "reagent solution" refers to a solution that contains the contents of Components A and B.

As used herein, "reagent system" refers to reagents that are used in the inventive assay, and include Components A and B either separately in an unmixed form or a mixed form.

As used herein, "sample" or "biological sample" or "biological specimen" is referred to in its broadest sense, and includes solid and liquid or any biological sample obtained from nature, including an individual, body fluid, cell line, tissue culture, or any other source. As indicated, biological samples include body fluids, such as blood, semen, lymph, sera, plasma, urine, synovial fluid, spinal fluid, sputum, pus, sweat, as well as liquid samples from the environment such as plant extracts, pond water and so on. Solid samples may include animal or plant body parts, including but not limited to hair, fingernail, leaves and so on.

Aldehyde Detection Reagent System

The present invention is directed to an aldehyde detection reagent system or a kit that includes at least two reagent components: a) Component A (pH from about 1.4 to 1.6): bisulfite, pararosaniline HCl, and hydrochloric acid; and b) Component B: a solution of hydroxide in water (pH of about 10-11).

The present invention is also directed to a combination of these components, as well as a mixture of these components to make one reagent solution containing the ingredients of these reagent components.

Component A

Regarding Component A, the pH level may be preferably from about 1.4 to 1.6. The sulfite included in Component A may be a metasulfite, preferably sodium sulfite or potassium sulfite. The amount of sulfite included may be preferably about 1 to 20 grams per liter of Component A; the amount of pararosaniline HCl (pararosaniline HCl hydrochloride or pararosaniline HCl acetate) included in Component A may be preferably in the range of about 1 to 10 grams per liter of Component A; the amount of HCl included in Component A may be about 0.017 to 1 mole per liter of Component A.

Bisulfite is a reducing agent that blocks chemical interference caused by oxygen in the atmosphere. The bisulfite condenses oxygen radicals, forcing the aldehydes to react only with pararosaniline HCl groups. Thus, the bisulfite also increases the storage time of the reagents by creating a nitrogenous atmosphere and canceling any reaction between the reagents and oxygen.

Pararosaniline HCl

The chemical structure of pararosaniline HCl shows that that it is missing a methyl group that is normally present on one of the aromatic rings in the chemical structure of basic fuchsin. Thus, basic fuchsin and pararosaniline HCl are structurally distinguished from each other. Pararosaniline HCl manufacturing processes are well known. A few widely used methods include:

(1) Exposing 4,4'-diaminodimethylmethane, aniline, aniline acid and nitrobenzene to heat in the presence iron chloride (III), and (2) Oxidizing p-aminobenzaldehyde and aniline by condensing them in acid and thus obtaining manganese dioxide as one of the products.

Pararosaniline HCl can be commercially purchased as well (National Aniline Div. Allied Chemical & Dye Corp., USA).

The pararosaniline HCl used in the present invention undergoes color changes relative to the amount of aldehyde present in a sample. Conventional reagents composed of fuchsin are known to react clearly and rapidly under an acidic environment. Pararosaniline HCl, however, reacts more strongly in neutral pH surroundings. The pararosaniline HCl containing reagent system used in the present invention changes rapidly from a colorless state to dark red when exposed to aldehyde in a neutral pH environment. Since test samples are generally in a neutral pH environment, it is expected that carrying out the aldehyde assay in neutral pH environment results in a more effective and efficient assay system.

According to the present invention, the pH of the hydrochloric acid may be stabilized and maintained at around a pH of about 1.4 to 1.7. Pararosaniline HCl remains most stable for longer periods of time under these conditions. Further, Component A may be stored in any container, such as a vial, ampoule and so on.

The amount of the reagents of Component A may vary as the test reagent system is optimized to detect aldehydes, and therefore, the invention is not bound by any indicated amount of a particular reagent that is merely exemplified in the present patent application. It is understood that the inventive reagent solution includes any amount of these individual reagents so long as aldehydes in the sample are detected.

Component B

Component B includes hydroxide in water. Preferably, sodium hydroxide is used. Typically, the range of pH for Component B reagent solution is about 11-12. Generally sodium hydroxide is included in Component B in about 0.1 to 10 grams per liter of water.

In the present invention, the hydroxide reagent solution of Component B may be mixed with Component A sometime before or shortly after contact with the test sample. Component B serves to neutralize and stabilize the acidity of Component A. By thus creating a neutral pH environment, reaction between pararosaniline HCl and aldehyde is permitted to take place.

Any sample that is suspected of containing aldehydes may be tested using this test reagent system. Bodily fluids such as urine and blood are two common samples. It is understood that other and all forms of biological or chemical fluids, including bodily fluids may be used in the practice of the invention.

The volumes of Component A, Component B or a reagent solution containing the contents of Components A and B used in reacting with a sample are not limited to any set amount, and may be adjusted according to the scale and purpose of the assay to be carried out. Therefore, it is understood that absolute amounts of the contents of the reagent solution is not important, so long as the reagent solution achieves aldehyde detecting function. Thus, the volume of the amount of Components A and B used may vary. For example, in one embodiment of the invention, a 1 ml urine sample may be mixed with 0.5 ml of Component A and 0.5 ml of Component B and the reaction run for about 5 minutes before reading the color of the reaction. In particular, and by way of example, Components A and B may be pre-mixed before contacting the reagent solution with the urine sample.

Kit

The inventive kit, which includes Components A and B of the reagent system described above, may in addition include the following items: (1) at least one container that contains the contents of Components A and B; (2) a sample container for collecting the test sample; (3) a sample transfer device such as a dropper, pipette, capillary pipette, micropipette, syringe, scoop, and so forth for transferring at least a measured or predetermined amount or portion of the sample from the sample container to another container for contact with the reagent solution to cause a reaction; and (4) a color table to be referred to for comparison with the color of the reaction after about 2 to 5 minutes.

In (1) above, it is understood that the reagent container may contain Components A and B separately or as mixed together. The contents of Components A and B may be mixed together in any order so long as the aldehyde detection function is retained. Once the reagent solution of neutral pH is formed, it is understood that the usable time for the assay kit may be limited since the chromogen pararosaniline HCl is not as stable in a neutral pH environment compared with an acidic environment. Thus if pre-mixed contents of Component A and Component B is included in the kit, the kit may set forth a time for expiration inscribed on the cover of the kit or the instruction communication.

Alternatively, Components A and B may be housed separately and may be mixed immediately before or after contacting the sample with the contents of Component A with instruction communication to mix them together before or after contact with the sample. This preserves the useful life of the reagent system.

The container for housing Component A, Component B or a reagent solution may include but is not limited to an ampoule, vial, bottle and the like. A container such as an ampoule may be hermetically sealed so as to be broken by breaking the seal, or the container may be sealed and resealed upon opening such as by a twist cap.

The container for collecting test sample may be any container at all, and may include for example, paper cup, plastic cup, bottle, container and so on, so long as it is useful for holding the contents of the sample until a part of its contents may be transferred to another container for testing or storage.

The sample transfer device may be any device, such as a dropper, pipette, micropipette, capillary pipette, syringe, scoop or any instrument at all as long as it effectively functions as a means of transporting the biological sample. The sample transfer device may be used to transfer a portion or a measured portion of the sample to either a container that already contains the reagent solution or a separate container to which the reagent solution may be added so that a reaction between the reagent solution and the sample takes place.

The color table may be designed to enable easy measurement by systematically organizing reaction colors.

Method of Detecting Presence of Aldehyde in a Sample

The present invention is directed to a method of detecting the presence and relative quantity of aldehyde in a test sample comprising: (i) making a reagent solution containing the contents of Components A and B; (ii) contacting the test sample with the reagent solution obtained in (i) to cause a reaction between the reagent solution and the aldehyde present in the test sample; and (iii) determining the presence or concentration of the aldehyde in the sample by comparing the reaction color with a color table after about 2 to 7 minutes of reaction.

In the process of making the reagent solution according to step (1) above, it is understood that in one aspect, the two components may be made separately and mixed thereafter to obtain the reagent solution. In such a case, the ratio of the two components A and B may be varied as long as the obtained reagent solution is at a neutral pH. The ratios of the volumes of Components A and B present in the reagent solution may be also varied, preferably about 1:0.8-1.2, respectively. The volume ratio may vary depending on the amount of reagents that are present in the components and the desired optimum reaction conditions.

The amount of the sample to be mixed with the reagent solution combination in step (ii) may be determined according to the type and condition of the specimen, within a level that maintains the overall pH neutrality of the test material. In a simplistic example, the amount of specimen present may be similar to the total amount of reagents present. Since the color reaction is carried out in a neutral pH environment, contrary to conventional test kits that employ acidic reaction environments, the test result is less affected by unexpected changes in pH.

In the process of using the inventive reagent system to detect the presence of aldehydes, step (iii) involves the determination of the concentration of aldehyde by comparing the color reaction results with a color table. The test results obtained may be compared to various standards, and may be measured visually or measurements obtained through optical machines such as a spectrophotometer.

Components A and B of the reagent system described above may be preferably stored separately in individual, sealed test-size ampoules or vials of conventional medical solution type or in any other type of packaged or unpackaged container. When packaged in such a manner and stored in a cool, dry place, the sealed bottles or vials have an expected shelf storage life of at least 12 months.

Alternatively, the contents of Components A and B may be mixed together and stored in individual, sealed test-size ampoules or vials of conventional medical solution type or in any other type of packaged or unpackaged container. The expected shelf storage life is about 2 years. However, if the reagent solution is sparged with an inert gas such as nitrogen gas before hermetically sealing its contents in an ampoule for instance, the useful life of the reagent solution may be lengthened.

In one embodiment of the invention, a positive aldehyde test may be performed by contacting a sample of known aldehyde-positive solutions with the reagent solution. In approximately 2-7 minutes, the solution should develop a reddish color. No color development indicates that the reagent solution is bad. The sensitivity of the aldehyde-positive solution and the reagent solution may be calibrated and designed for optimum accuracy.

Pararosaniline HCl reacts with aldehydes present in biological specimen such as skin, urine or blood plasma. With low or no aldehydes present, there is no color development. With moderate or high levels of aldehydes, color gradations are roughly dependent on the level of aldehydes present. The amino group of pararosaniline HCl couples with the aldehyde to produce the reddish color approximately dependent on the amount of aldehyde present in the biological specimen.

It is generally contemplated that the concentration of aldehyde-modified chromogen can be visually (i.e., in a non-automated manner) determined, for example, by employing a reference chart which may be part of a test kit. Contemplated reference charts may thereby include a relative or arbitrary readout, or a semi-quantitative or quantitative readout. Alternatively, it is contemplated that the determination of the presence of aldehyde in a test sample may include an at least partially automated routine, and particularly contemplated routines may include a spectrophotometer (single or multiple wave length).

It is also generally contemplated that aldehydes and in particular malondialdehyde (MA) and other related aldehydes are released from the breakdown of long chain polyunsaturated fatty acids by free radical attack. Interestingly, high levels of MDA and related aldehydes are found in a variety of diseases and disease states other than oxidative stress. Therefore, it should be especially appreciated that the methods and compositions according to the inventive subject matter may also be useful in detecting and/or confirming abnormal metabolism states, including coronary artery disease, type-1 and type-2 diabetes, and Parkinson disease.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

EXAMPLE

Example 1

Directions for Using Pararosaniline HCl Aldehyde Test Kit

Make Component A by using 7.69 grams of sodium metasulfite, 7.69 grams pararosaniline HCl, and 0.17 mol in one liter. The pH of the solution is about 1.4 to 1.6. Component B is made by adding 0.37 grams of sodium hydroxide in 1 liter of deionized water. The pH of the solution is about 11-12.

Fill a cup with a urine sample to be tested. Draw 1 ml urine into a dropper tube up to a designated line. Break off the top of an ampoule containing the reagent solution containing 0.5 ml of Component A and 0.5 ml of Component B. Squeeze the urine in the dropper into the broken ampoule containing the reagent solution. Wait about 2 to 7 minutes, then hold the ampoule up to an evaluation chart to match colors. Record the reading on a record card. It is preferred that the test be performed when the urine is substantially free of debris.

The evaluation chart may indicate the level of free radical activity in the test sample. In the free radical test, certain gradations may be made so that if the color is clear for example it may label this color grade as being optimum. The next color grade may be labeled low free radical activity, the next grade may be labeled medium free radical activity and the next grade may be labeled as showing high free radical activity.

Antioxidants, such as vitamin E, C and so on may address some free radical problems present within a person. Other antioxidants may be used that are known in the art to decrease the level of free radicals present in a person once such level is detected.

Example 2

Comparative Thermal Stability Measurements

Thermal stability of the inventive reagent solution and a commercially available test kit marketed by Vespro Life Sciences (Olathe, Kans.) (hereafter referred to as "I") was determined and compared.

inventive components A and B, the combination of which forms the inventive reagent solution (hereafter referred to as "II") were used for comparative measurement. A cup was filled with a urine sample to be tested. 1 ml urine was drawn into a dropper tube up to a designated line and discharged into a vial. The tops of ampoules containing 0.5 ml of Component A and 0.5 ml of Component B were broken and their contents discharged into the vial. After about 2 to 7 minute wait, vial was held up to an evaluation chart to match colors. The readings were recorded. It is preferred that the test be performed when the urine is substantially free of debris.

The solutions were assayed for change in color from clear to pink in a water bath set at 30° C. and 40° C. In the case of commercial kit (I), after 20 minutes the color changed to pink in 30° C. water bath and after 10 minutes the color changed to pink in 40° C. water bath. In contrast, the inventive reagent solution (II) showed no color change after 5 hours of incubation in both 30° C. and 40° C. water baths. This indicates that the inventive reagent solution is advantageously stable to temperature over a longer period of time than the commercially available kit (I).

Example 3

Comparative pH Stability Measurements

The pH stability of solutions I and II described in Example 2 was determined. 1% diluted hydrochloric acid and 1% diluted sodium hydroxide solution were added to I and II, and checked for change in color. When 1% sodium hydroxide solution was added to solution I, the color changed to pink, but no color difference was detected when hydrochloric acid was added. In contrast, the inventive reagent solution (II) displayed no color change when hydrochloric acid or sodium hydroxide was added. This indicates that the inventive reagent solution is advantageously more stable to pH fluctuations than kit I.

Those skilled in the art will recognize, or be able to ascertain using no more than routine experimentation, many: equivalents to the specific embodiments of the invention specifically described herein. Such equivalents are intended to be encompassed in the scope of the claims.

What is claimed is:

1. A system for detecting presence of aldehyde in a sample, said system comprising:
   (i) Component A, which comprises bisulfite, pararosaniline HCl, and hydrochloric acid;
   (ii) Component B, which comprises a solution of hydroxide, wherein the Component A has a pH of from about 1.4 to 1.6 and the pH of the combined solution of Component A and Component B is neutral; and
   (iii) a urine sample suspected of containing aldehydes.

2. The system according to claim 1, wherein the bisulfite is sodium bisulfite and is present in an amount of about 1 to 20 grams per liter of Component A.

3. The system according to claim 1, wherein the pararosaniline HCl is present in a range of about 1 to 10 grams per liter of Component A.

4. The system according to claim 1, wherein the hydrochloric acid is present in about 0.017 to 1 mole per liter of Component A.

5. The system according to claim 1, wherein the hydroxide is sodium hydroxide and is present in about 0.1 to 10 grams per liter of water in Component B.

6. The system according to claim 1, wherein the aldehyde is malondialdehyde.

7. The system of claim 1, wherein the bisulfite is sodium bisulfite and is present in about 0.5 to 10 grams per liter of the combined solution of Component A and Component B.

8. The system of claim 1, wherein the pararosaniline HCl is present in about 0.5 to 5 grams per liter of the combined solution of Component A and Component B.

9. A kit for detecting presence of aldehyde in a urine sample, said kit comprising:
   (i) at least one reagent container comprising Component A, having a pH of from about 1.4 to 1.6 and which comprises bisulfite, pararosaniline HCl, and hydrochloric acid and Component B, which comprises a solution of hydroxide, and wherein the combined solution of Component A and Component B has neutral pH;
(ii) a container for collecting a urine sample;
(iii) a sample transfer device for transferring a portion of the sample from the container to another container for reaction with the reagent solution; and
(iv) a color table to be referred to for comparison with the color of the reaction.

10. The kit according to claim 9, wherein Component A and Component B are pre-mixed.

11. The kit according to claim 10, further comprising an expiration date on the kit.

12. The kit according to claim 9, wherein from about 0.2 to 2 ml of Component A and about 0.2 to 2 ml of Component B are contained in the reagent container.

13. The kit according to claim 9, wherein Components A and B are present in a 1:0.8~1.2 volume ratio, respectively.

14. A method for detecting presence of aldehyde in a test sampled, said method comprising
(i) making a neutral pH reagent solution comprising Component A, having a pH of from about 1.4 to 1.6 and which comprises bisulfite, pararosaniline HCl, and hydrochloric acid and Component B, which comprises a solution of hydroxide;
(ii) contacting a urine sample suspected of containing aldehydes with the reagent solution in (i) to form a reaction; and
(iii) determining the presence of the aldehyde in the sample by comparing the color of the reaction with a color table.

15. The method according to claim 14, wherein the reaction color is read at between about 2 to 7 minutes.

16. The method according to claim 14, wherein the aldehyde is malondialdehyde.

* * * * *